United States Patent
Huang et al.

(10) Patent No.: US 11,774,335 B2
(45) Date of Patent: Oct. 3, 2023

(54) EXPERIMENTAL SYSTEM OF SURROUNDING ROCK AND LINING STRUCTURE UNDER UNEQUAL SURROUNDING PRESSURE AND WATER PRESSURE

(71) Applicant: CHANGJIANG RIVER SCIENTIFIC RESEARCH INSTITUTE, CHANGJIANG WATER RESOURCES COMMISSION, Wuhan (CN)

(72) Inventors: Shuling Huang, Wuhan (CN); Xiuli Ding, Wuhan (CN); Shan Li, Wuhan (CN); Yuting Zhang, Wuhan (CN); Jun He, Wuhan (CN); Dengxue Liu, Wuhan (CN); Gang Han, Wuhan (CN); Peiyang Yu, Wuhan (CN)

(73) Assignee: CHANGJIANG RIVER SCIENTIFIC RESEARCH INSTITUTE, CHANGJIANG WATER RESOURCE COMMISSION, Wuhan (CN)

(*) Notice: Subject to any disclaimer, the term of this patent is extended or adjusted under 35 U.S.C. 154(b) by 0 days.

(21) Appl. No.: 17/967,864

(22) Filed: Oct. 17, 2022

(65) Prior Publication Data
US 2023/0060186 A1    Mar. 2, 2023

(30) Foreign Application Priority Data
Aug. 17, 2021  (CN) .......................... 202110943798.3

(51) Int. Cl.
*G01N 3/12* (2006.01)

(52) U.S. Cl.
CPC ....... *G01N 3/12* (2013.01); *G01N 2203/0048* (2013.01)

(58) Field of Classification Search
CPC .......................... G01N 3/12; G01N 2203/0048
USPC .......................................................... 405/153
See application file for complete search history.

(56) References Cited

FOREIGN PATENT DOCUMENTS

| CN | 105547849 A | * | 5/2016 | .......... G01N 15/082 |
| CN | 110346216 A | * | 10/2019 | .............. G01N 1/08 |
| CN | 112268768 A | * | 1/2021 | .............. G01N 1/28 |
| CN | 112284922 A | * | 1/2021 | |
| CN | 112378793 A | * | 2/2021 | .............. G01N 3/02 |
| CN | 112557203 A | * | 3/2021 | ......... G01N 15/0826 |
| CN | 111982692 B | * | 7/2021 | .............. G01N 3/12 |

* cited by examiner

*Primary Examiner* — Marrit Eyassu

(57) ABSTRACT

The invention discloses an experimental system of surrounding rock and lining structure under unequal surrounding pressure and water pressure, comprising: reaction wall, lining structure, external water pressure loading mechanism, internal water pressure loading mechanism, prestress-loading mechanism, surrounding rock layer and monitoring device. The Experimental System can simulate the stress characteristics and related deformation characteristics of the surrounding rock of the tunnel and the lining structure of the water conveyance tunnel under complex internal and external loads in the actual environment, and can help to analyze and study the broken appearance of the lining structure and the crack distribution after cracking.

8 Claims, 7 Drawing Sheets

EXPERIMENTAL SYSTEM OF SURROUNDING ROCK AND LINING STRUCTURE UNDER UNEQUAL SURROUNDING PRESSURE AND WATER PRESSURE

CROSS REFERENCE OF RELATED APPLICATIONS

This patent application claims the benefit and priority of Chinese Patent Application No. 202110943798.3 filed on Aug. 17, 2021, the disclosure of which is incorporated by reference herein in its entirety as part of the present application.

TECHNICAL FIELD

The invention relates to the technical field of long distance water conveyance tunnel test structure model, in particular to an experimental system of surrounding rock and lining structure under unequal surrounding pressure and water pressure.

BACKGROUND

With the continuous improvement of the country's comprehensive national strength, the national infrastructure construction has developed rapidly. Deep buried long tunnels are constantly emerging in the construction of various large-scale underground projects in China. During the construction process, underground space is generated due to excavation. However, the excavation of the project destroys the balance of the original initial geostress of the rock mass, resulting in a series of complex rock mechanics. On the one hand, the natural equilibrium state of rock mass is affected by excavation, resulting in rock cracks. The rock mass around the tunnel will continue to expand and deform towards the rock mass excavation damage, leading to the formation of new stress state in the surrounding rock. If the new stress distribution of the surrounding rock exceeds the bearing capacity of the rock mass, the surrounding rock will be damaged, and the deformation and destruction of the surrounding rock will impose unequal surrounding rock pressure from different directions on the lining structure; On the other hand, in the pressure tunnel, there is a high internal water pressure, which is transmitted to the surrounding rock through the lining structure; The surrounding rock has a high external water pressure, which penetrates into the lining structure through the surrounding rock layer. In order to prevent these complex unequal surrounding rock pressures and internal and external water pressures from damaging the integrity of the surrounding rock lining structure and causing its instability, it is necessary to conduct in-depth research on the stress characteristics of the surrounding rock lining structure of the tunnel to ensure the stable operation of the tunnel.

It is very important to find effective test methods and corresponding test devices and to monitor and test their structural forms and mechanical properties. At present, the mechanical monitoring test of the water conveyance tunnel is mostly conducted by numerical simulation method, which is difficult to simulate the stress of the surrounding rock of the tunnel and the lining structure of the water conveyance tunnel in the actual environment.

Although there are also some simulation test methods, there are some drawbacks. First, the stability and sealing of the test device often fail to meet the design requirements, which make it difficult to load the external water pressure or surrounding rock pressure to the required value, and cannot reflect the stress characteristics and related deformation characteristics of the surrounding rock lining structure under real complex loads. Therefore, it is not easy to conduct research on the failure form of the lining structure and the crack distribution after cracking; Secondly, the existing surrounding rock layer is mostly poured with ordinary concrete, which can not reflect the crack distribution of the real surrounding rock structure, and even if the required external water pressure is loaded, it cannot simulate the seepage characteristics of the real surrounding rock structure, and the water pressure cannot be well transmitted to the lining structure, causing test errors; Third, some of the existing test methods use external water pressure to simulate the surrounding rock pressure, which directly acts on the lining structure to load the surrounding rock pressure, which is inconsistent with the actual loading mode of the lining. Therefore, it is necessary to develop a test method that can simulate the surrounding rock and lining structure under unequal confining pressure and internal and external water pressure, so as to realize the simulation that the surrounding rock and lining jointly bear complex water pressure and unequal surrounding rock pressure, and to study the mechanical properties, broken characteristics and stability of the surrounding rock lining structure under the independent or combined action of internal and external water pressure and unequal surrounding rock pressure.

SUMMARY

The purpose of the invention is to truly simulate the mechanical properties, failure characteristics and stability of the surrounding rock lining structure of a long-distance water conveyance tunnel under the independent or combined action of internal and external water pressures and unequal surrounding rock pressures, and to provide an experimental system of surrounding rock and lining structure under unequal surrounding pressure and water pressure.

To achieve the above purpose, the experimental system of surrounding rock and lining structure under unequal surrounding pressure and water pressure, comprising:

reaction wall with a three-dimensional hollow shell structure; the center of the inner cavity of reaction wall is provided with a vertically arranged hollow cylindrical lining structure, and the height of the lining structure is the same as the height of the inner cavity of reaction wall, so that the circumferential inner wall of reaction wall and the outer wall of lining structure form an external pressure chamber, and the inner top and inner bottom of reaction wall and the inner wall of lining structure form an internal water injection pressure chamber;

the outer wall of the lining structure is provided with a surrounding rock layer of pervious concrete's structure; a prestress-loading mechanism is arranged inside the surrounding rock layer; the prestress-loading mechanism consists of prestress steel strand, which compresses the surrounding rock layer in four directions, left and right, front and back through the prestress steel strand, to simulate the effect of the unequal surrounding rock pressure outside the tunnel;

an external water pressure loading mechanism is also arranged outside the opening end of the reaction wall; the surrounding rock layer and the lining structure are applied with external water pressure in the direction of periphery to the center via the external water pressure loading mechanism, to simulate the effect of the external water pressure of the tunnel; an internal water pressure loading mechanism is arranged on the reaction wall corresponding to the upper end of the hollow cylinder of the lining structure; the internal water pressure loading mechanism is used to inject water into the internal water injection pressure chamber for pressurization, to simulate the effect of the internal water pressure of the tunnel;

the experimental system also includes a monitoring device embedded in the surrounding rock layer and lining structure respectively; the monitoring device is used to collect and analyze the following data: the surrounding rock pressure in the surrounding rock layer, the internal and external water pressure, and the stress and strain in the lining structure.

In the embodiment of the invention, the surrounding rock layer is arranged with a disposable pervious concrete structure and a circulating pervious concrete structure from the inside to the outside;

the disposable pervious concrete structure is a cuboid structure attached to the outside of the lining structure, and the circulating pervious concrete structure is a cuboid structure attached to the outside of the disposable pervious concrete structure;

the disposable pervious concrete structure comprises a first cushion layer, a first stress layer, a second stress layer, a third stress layer and a second cushion layer arranged from the lower end to the upper end; a lubrication layer is respectively arranged between the first cushion layer and the first stress layer, and between the third stress layer and the second cushion layer of the disposable pervious concrete structure; a mortar layer is respectively arranged between the first stress layer and the second stress layer, and between the second stress layer and the third stress layer of the disposable pervious concrete structure;

the circulating pervious concrete structure comprises a first cushion layer, an overall stress layer and a second cushion layer arranged from the lower end to the upper end; a lubrication layer is respectively arranged between the first cushion layer and the overall stress layer, and between the overall stress layer and the second cushion layer of the circulating pervious concrete structure; the overall stress layer of the circulating pervious concrete structure is located outside the first stress layer, the second stress layer and the third stress layer of the disposable pervious concrete structure; two # shaped steel strand channels are chiseled inside the overall stress layer of the circulating pervious concrete structure, which are arranged in two layers; the outer wall of t the overall stress layer of the circulating pervious concrete structure is bonded with heavy plate for force transmission.

In the embodiment of the invention, the prestress-loading mechanism includes eight prestress steel strands running through the # shaped steel strand duct; the end of each prestress steel strand is fixed outside the heavy plate for force transmission; the eight prestress steel strands are tensioned through the hydraulic tensioner, the pressure is measured by the tension sensor connected to the prestress steel strand; the hydraulic tensioner is connected with oil pressure gauge and electric high-pressure oil pump through oil pipe.

In the embodiment of the invention, the lining structure comprises hollow barrel and flange plate arranged at the upper and lower ends thereof; the hollow inner diameter of the hollow barrel is the same as the inner diameter of the flange plate; the outer side of the hollow barrel is provided with grouting zone from the lower end to the upper end, and the outer diameter of the grouting zone is the same as the outer diameter of the flange plate.

In the embodiment of the invention, the reaction wall comprises a reaction wall body of a three-dimensional hollow shell structure with an opening at one end and a boss on the inner wall of the opening, a rubber seal groove is arranged on the boss along the periphery of the opening, a sealing steel plate is matched and arranged in the rubber seal groove, an upper cover plate is arranged outside the sealing steel plate, which is bolted to the reaction wall body, and the upper cover plate is also connected with the sealing steel plate by bolts; the center of the lower bottom surface of the inner cavity of the reaction wall body is fixedly provided with a locating steel ring, and the inner diameter of the locating steel ring is the same as the outer diameter of the flange plate.

In the embodiment of the invention, the outer peripheral wall of the reaction wall body is provided with first stiffener in a crisscross structure, and the outer edges around the opening end of the reaction wall body are respectively provided with first bolt holes for connecting with the upper cover plate; the center of the sealing steel plate is provided with a water injection valve gate, second bolt holes connected with the lining structure is arranged around the water injection valve gate, and a second instrument cable outlet is also arranged on one side of the water injection valve gate; the upper cover plate comprises a second stiffener in a crisscross structure arranged on the outer surface, a second water injection valve connector corresponding to the water injection valve gate is arranged at the center of the upper cover plate, third bolt holes corresponding to the second bolt holes is arranged around the second water injection valve connector, and a fourth instrument cable outlet corresponding to the second instrument cable outlet is arranged on one side of the second water injection valve connector, fourth bolt holes corresponding to the first bolt holes is also arranged at the peripheral edge of the upper cover plate; fifth bolt holes corresponding to the second bolt holes is arranged around the flange plate at the upper end of the lining structure, and a rubber seal ring is used between the flange plate at the upper end and the sealing steel plate for sealing; the side wall of the reaction wall body is provided with a first water injection valve connector, and the another side wall opposite to the first water injection valve connector is provided with a drain valve connector.

The invention also provides an experimental method of surrounding rock and lining structure under unequal surrounding pressure and water pressure, comprising the following steps:

Step 1) Pour to form the lining structure and surrounding rock layer with the same height, wherein, pouring the lining structure includes: binding the reinforcement cage of lining structure according to the design size; Pouring and curing of lining structure with concrete meeting the required design strength; and embedding the detector at the position to be detected in the lining structure;

Pouring the surrounding rock layer includes: pouring the surrounding rock layer into a specific shape and curing according to the design template, embedding the detector at the position to be detected to be detected in the surrounding rock layer, reserving the # shaped steel strand duct in the surrounding rock layer, and distributing the # shaped steel strand duct around the lining structure;

Step 2) Install the prestress-loading mechanism, including: first fix the lining structure that has been poured and cured, and then closely stick the surrounding rock layer that has been poured and cured to the outer wall of the lining structure and building with mortar; After the mortar is solidified, embed four heavy plates for force transmission around the surrounding rock layer; and drill holes on the heavy plate corresponding to the extension of the prestress steel strand; Pass four prestress steel strands through the # shaped steel strand duct reserved in the surrounding rock layer, and fix the end of each prestress steel strand outside the heavy plate; Tension the prestress steel strand through the hydraulic tensioner and the electric high-pressure oil pump, and fix both ends of the prestress steel strand with the anchorage when the predetermined tensile stress is reached;

Step 3) Lift the whole body formed by lining structure and surrounding rock layer together with prestress steel strand vertically into the inner cavity of reaction wall, and insert the bottom of lining structure into locating steel ring;

Step 4) Install and seal the upper cover plate, including: install a rubber seal ring at the boss of the opening of the reaction wall body and the top of the lining structure; cover the upper cover plate on the sealing steel plate, connect the lining structure with the sealing steel plate and the upper cover plate by bolts, and connect the reaction wall body with the upper cover plate by bolts; In addition, the data line of detector embedded in lining structure and the data line of detector embedded in surrounding rock layer are led out through the second instrument cable outlet of the sealing steel plate and the fourth instrument cable outlet of the upper cover plate;

Step 5) Install the external water pressure loading mechanism, including: install the second pipe on the first water injection valve connector outside the reaction wall body, and install the second booster pump and the second water pressure gauge on the other end of the second pipe;

Step 6) Install the internal water pressure loading mechanism, including: install the first pipe on the second water injection valve connector outside the upper cover plate, and install the first booster pump and the first water pressure gauge on the other end of the first pipe;

Step 7) load the external water pressure, including: seal the second instrument cable outlet, the fourth instrument cable outlet and the sealing steel plate around; according to the experimental scheme, open the second booster pump to Inject water into the external pressure chamber formed between the circumferential inner wall of reaction wall and the outer wall of lining structure;

Step 8) load the internal water pressure, including: seal the lining structure; according to the experimental scheme, open the first booster pump to inject water into the internal water injection pressure chamber formed between the inner wall of lining structure and reaction wall, Until the water pressure reaches the set design value, use the data acquisition instrument to collect data;

Step 9) Connect the data line of the detector to the data acquisition instrument for data acquisition, and then connect it to the computer; Through the data acquisition software, collect and post process the collected stress and strain, pressure of prestress steel strand, internal and external water pressure and other data, and analyze the stability of surrounding rock layer under different pressure loads and the stress and strain relationship between steel bars and concrete in lining structure.

Preferably, in the Step 8), the second instrument cable outlet and the fourth instrument cable outlet are filled and sealed with epoxy resin; and the connection between the sealing steel plate and the reaction wall body is fully welded.

More preferably, the bottom of the lining structure is sealed by pouring 40-60 mm thick epoxy resin at the bottom of the lining structure; The inner wall of the lining structure is sealed by placing PVC pipe in the lining structure, and then filling epoxy resin between the inner wall of the lining structure and the PVC pipe; the diameter of the PVC pipe is slightly smaller than the inner diameter of lining structure.

THE BENEFICIAL EFFECTS OF THE INVENTION

1. This Experimental System can apply unequal surrounding rock pressure and internal and external water pressure independently or simultaneously, and the prestress-loading mechanism can exert different pressures on the left, right, front and rear directions of the surrounding rock layer at the same time, which is more consistent with the real stress state of surrounding rock and lining structures such as long-distance water conveyance tunnels and highway and railway tunnels.

2. The Experimental System is sealed with flange, rubber seal ring, sealing steel plate and other components, which can better maintain the internal and external water pressure and better simulate the effect of internal and external water pressure on the lining structure.

The Experimental System of the invention can simulate the stress characteristics and related deformation characteristics of the surrounding rock of the tunnel and the lining structure of the water conveyance tunnel under complex internal and external loads in the actual environment, and can help to analyze and study the broken appearance of the lining structure and the crack distribution after cracking.

Figure 1:
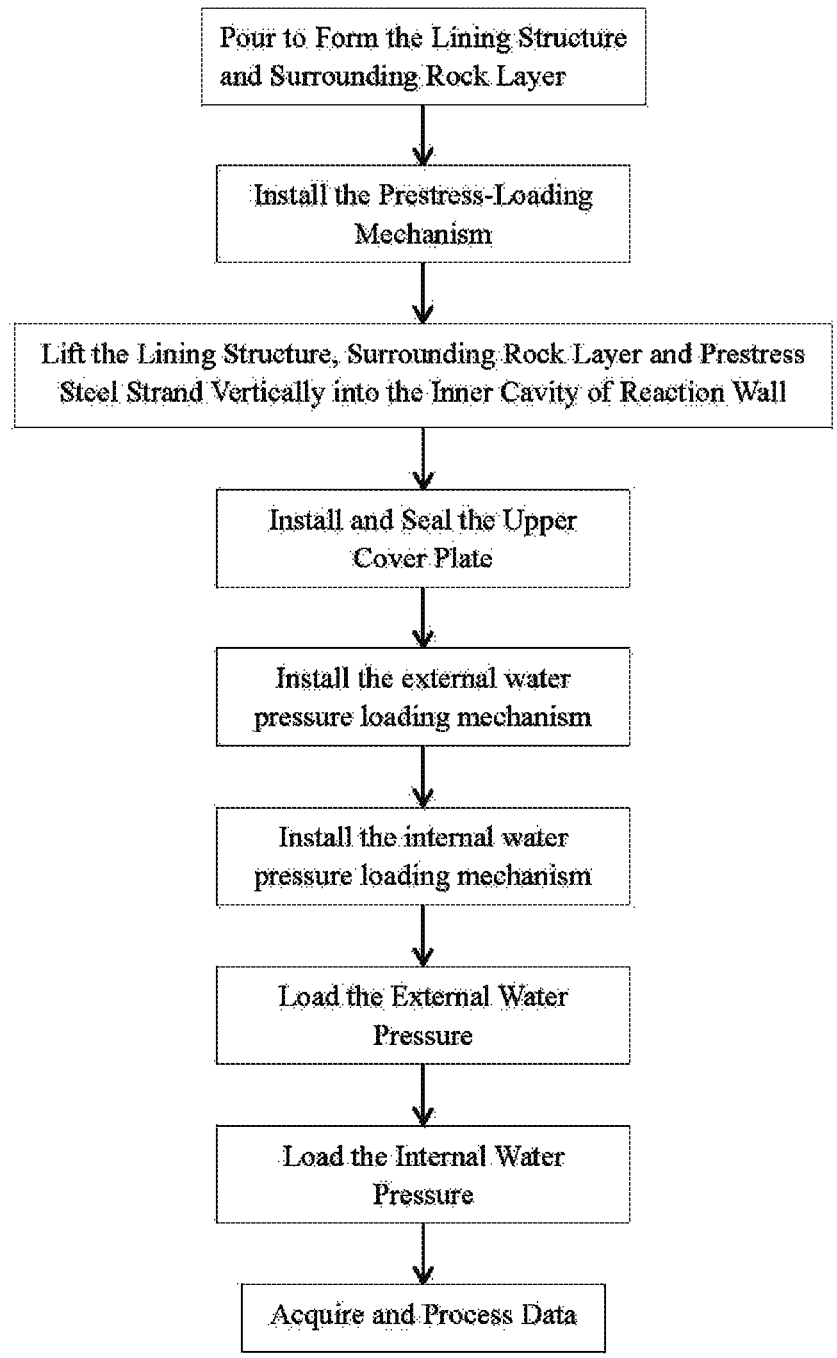
FIG. 1 is the flow chart of the Experimental System of the present invention.
Figure 2:
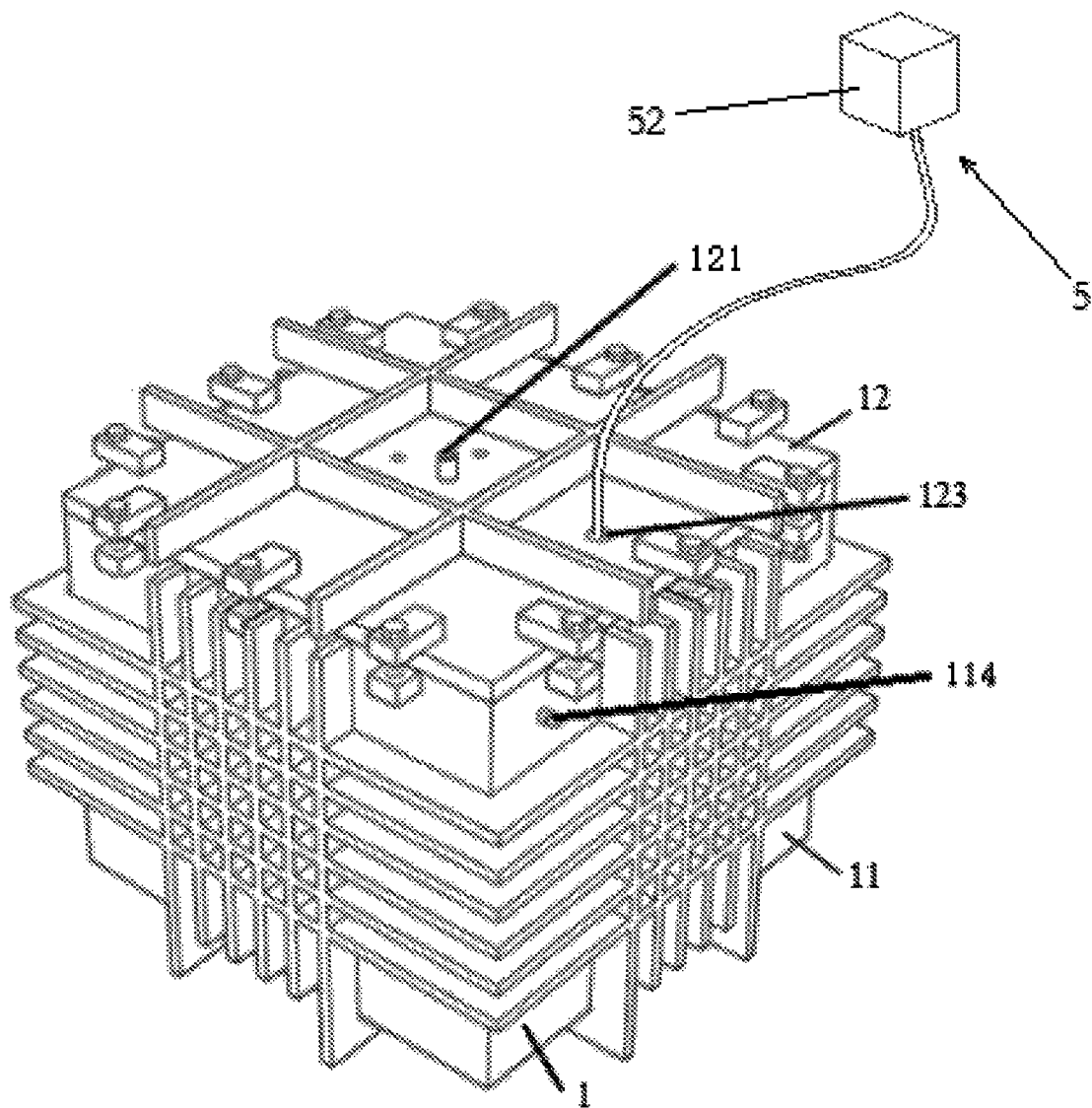
FIG. 2 shows the overall external structure diagram of the Experimental System of the present invention.

In the above figure, the Experimental System of the present invention includes reaction wall 1, lining structure 2, internal water pressure loading mechanism 31, external water pressure loading mechanism 33, unequal surrounding rock pressure steel strand prestress-loading mechanism 32, surrounding rock layer 4, monitoring system 5;

The reaction wall 1 includes: reaction wall body 11, upper cover plate 12, sealing steel plate 13;

The reaction wall body 11 includes: first bolt holes 112, first stiffener 113, first water injection valve connector 114, drain valve connector 115, rubber seal groove 116, and locating steel ring 111;

The upper cover plate 12 includes: third bolt holes 122, fourth instrument cable outlet 123, fourth bolt holes 124, second stiffener 125, and second water injection valve connector 121;

The sealing steel plate 13 includes: water injection valve gate 131, second bolt holes 132, and second instrument cable outlet 133;

The lining structure 2 includes: hollow barrel 21, flange plate 22, fifth bolt holes 221, grouting ring 23;

The internal water pressure loading mechanism 31 includes: first booster pump 311, first water pressure gauge 312, and first pipe 313;

The external water pressure loading mechanism 33 includes: second booster pump 331, second water pressure gauge 332, and second pipe 333;

The prestress-loading mechanism 32 includes: prestress steel strand 321, hydraulic tensioner 322, electric high-pressure oil pump 323, tension sensor 324, anchorage 325, oil pressure gauge 326, oil pipe 327, and heavy plate 328;

The surrounding rock layer 4 includes: disposable pervious concrete structure 41, circulating pervious concrete structure 42, mortar layer 43, lubricating layer 44, # shaped steel strand duct 45;

The monitoring device 5 includes detector 51 and data acquisition instrument 52.

DETAILED DESCRIPTION OF THE EMBODIMENTS

In order to make the purpose, technical scheme and advantages of the embodiments of the invention more clear, the technical scheme in the embodiments of the invention will be described clearly and completely below in combination with the drawings in the embodiments of the invention. Obviously, the described embodiments are part of the embodiments of the invention, not all of them. Based on the embodiments of the invention, all other embodiments obtained by ordinary technicians in the art without creative work belong to the scope of the invention.

In the description of the invention, it should be understood that the terms "length", "width", "top", "bottom", "front", "back", "left", "right", "vertical", "horizontal", "top", "bottom", "inside", "outside" and other directions or positional relationships indicated are based on the directions or positional relationships shown in the drawings, only for the convenience of describing the invention and simplifying the description, Rather than indicating or implying that the device or element referred to must have a specific orientation, be constructed and operate in a specific orientation, it cannot be understood as a limitation on the invention.

Embodiment

Experimental System of the present invention, as shown in FIGS. 2 to 10, includes reaction wall 1 with a three-dimensional hollow shell structure. The center of the inner cavity of reaction wall 1 is provided with a vertically arranged hollow cylindrical lining structure 2, and the height of the lining structure 2 is the same as the height of the inner cavity of reaction wall 1, so that the circumferential inner wall of reaction wall 1 and the outer wall of lining structure 2 form an external pressure chamber, and the inner top and inner bottom of reaction wall 1 and the inner wall of lining structure 2 form an internal water injection pressure chamber.

The outer wall of the lining structure 2 is provided with a surrounding rock layer 4 of pervious concrete's structure. A prestress-loading mechanism 32 is arranged inside the surrounding rock layer 4. The prestress-loading mechanism 32 consists of prestress steel strand 321, which compresses the surrounding rock layer 4 in four directions, left and right, front and back through the prestress steel strand 321, to simulate the effect of the unequal surrounding rock pressure outside the tunnel.

An external water pressure loading mechanism 33 is also arranged outside the opening end of the reaction wall 1. The surrounding rock layer 4 and the lining structure 2 are applied with external water pressure in the direction of periphery to the center via the external water pressure loading mechanism 33, to simulate the effect of the external water pressure of the tunnel; an internal water pressure loading mechanism 31 is arranged on the reaction wall 1 corresponding to the upper end of the hollow cylinder of the lining structure 2. The internal water pressure loading mechanism 31 is used to inject water into the internal water injection pressure chamber for pressurization, to simulate the effect of the internal water pressure of the tunnel;

The Experimental System also includes a monitoring device 5 embedded in the surrounding rock layer 4 and lining structure 2 respectively. The monitoring device 5 is used to collect and analyze the following data: the surrounding rock pressure in the surrounding rock layer 4, the internal and external water pressure, and the stress and strain in the lining structure 2.

Preferably, the surrounding rock layer 4 is arranged with a disposable pervious concrete structure 41 and a circulating pervious concrete structure 42 from the inside to the outside. The disposable pervious concrete structure 41 is a cuboid structure attached to the outside of the lining structure 2, and the circulating pervious concrete structure 42 is a cuboid structure attached to the outside of the disposable pervious concrete structure 41; The disposable pervious concrete structure 41 comprises a first cushion layer, a first stress layer, a second stress layer, a third stress layer and a second cushion layer arranged from the lower end to the upper end. A lubrication layer 44 is respectively arranged between the first cushion layer and the first stress layer, and between the third stress layer and the second cushion layer of the disposable pervious concrete structure 41; a mortar layer 43 is respectively arranged between the first stress layer and the second stress layer, and between the second stress layer and the third stress layer of the disposable pervious concrete structure 41; The circulating pervious concrete structure 42 comprises a first cushion layer, an overall stress layer and a second cushion layer arranged from the lower end to the upper end. A lubrication layer 44 is respectively arranged between the first cushion layer and the overall stress layer, and between the overall stress layer and the second cushion layer of the circulating pervious concrete structure 42. The overall stress layer of the circulating pervious concrete structure 42 is located outside the first stress layer, the second stress layer and the third stress layer of the disposable pervious concrete structure 41. Two # shaped steel strand channels 45 are chiseled inside the overall stress layer of the circulating pervious concrete structure 42, which are arranged in two layers. The outer wall of t the overall stress layer of the circulating pervious concrete structure 42 is bonded with heavy plate 328 for force transmission.

The surrounding rock layer 4 is made of C10 pervious concrete. The disposable pervious concrete structure 41 of the inner circle of the whole surrounding rock layer 4 consists of 5 layers (from the lower end to the upper end, they are: first cushion layer, first stress layer, second stress layer, third stress layer, and second cushion layer), each layer is spliced with 4 pervious concrete blocks, a total of 20 pieces. The circulating pervious concrete structure 42 of the outer circle of the surrounding rock layer 4 consists of 3 layers (from the lower end to the upper end, they are: the first cushion layer, the overall stress layer, and the second cushion layer), each layer is spliced with 4 pervious concrete blocks, a total of 12 pieces.

Figure 6:
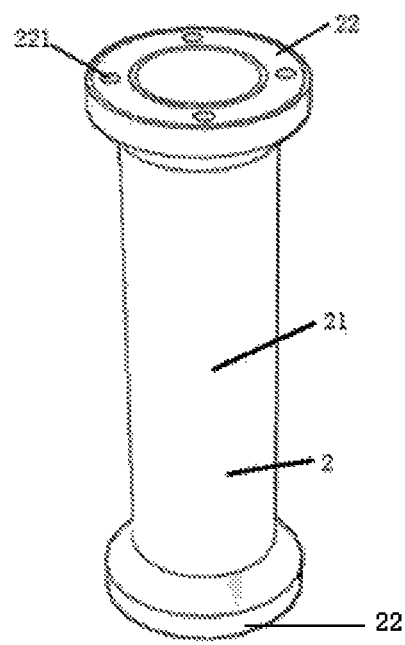
FIG. 6 is the structural diagram of the lining structure in FIG. 2.
Figure 7:
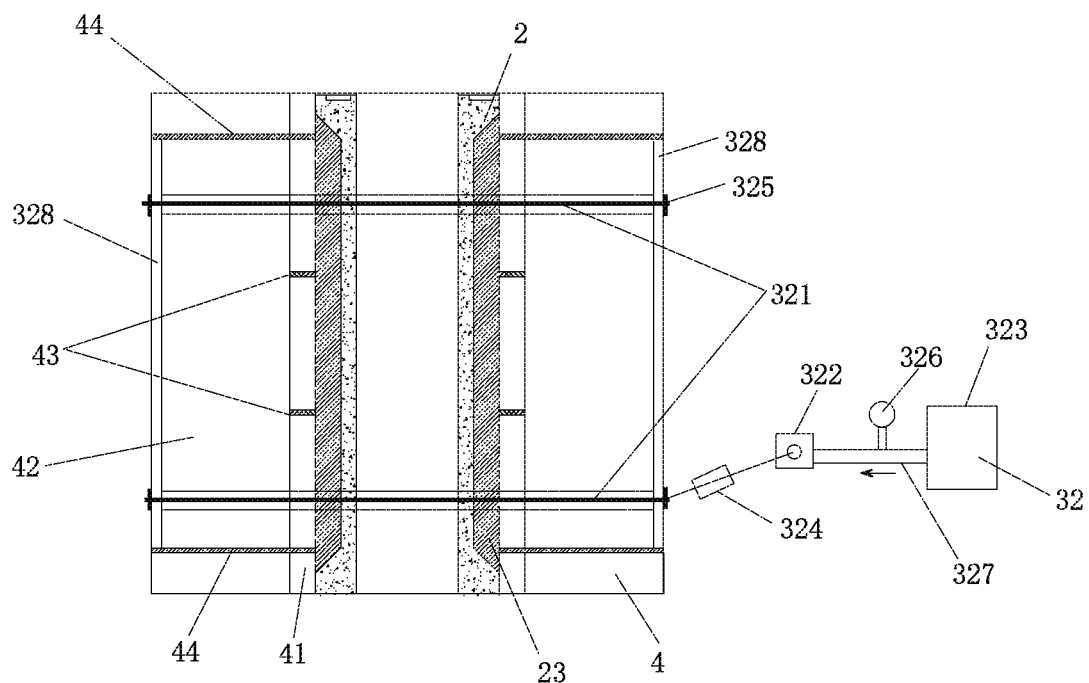
FIG. 7 is the installation structure diagram of the prestress-loading mechanism of the invention.
Figure 8:
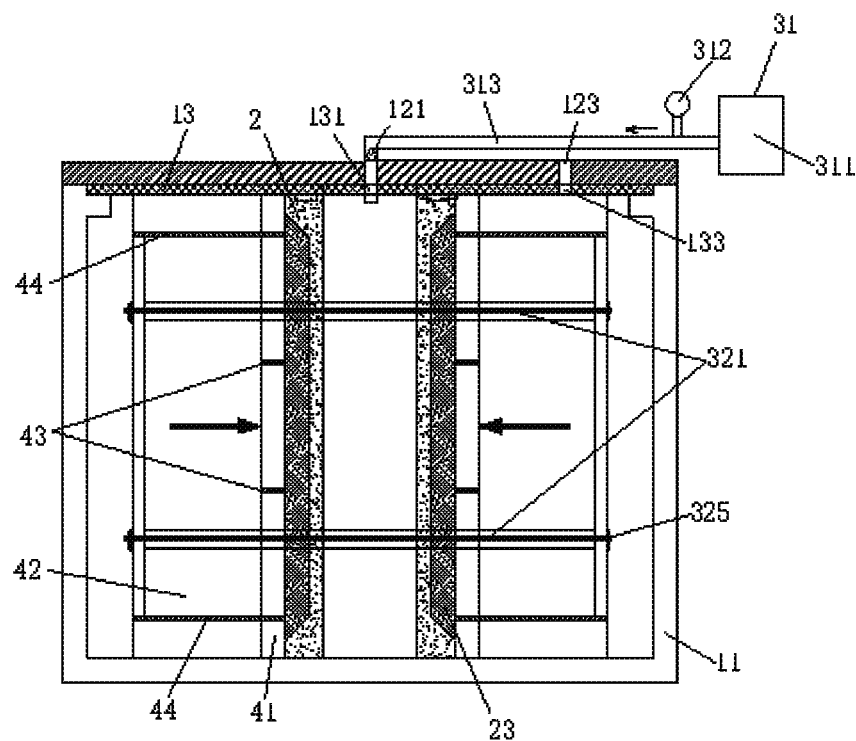
FIG. 8 is the vertical sectional structure diagram of FIG. 2.
Figure 9:
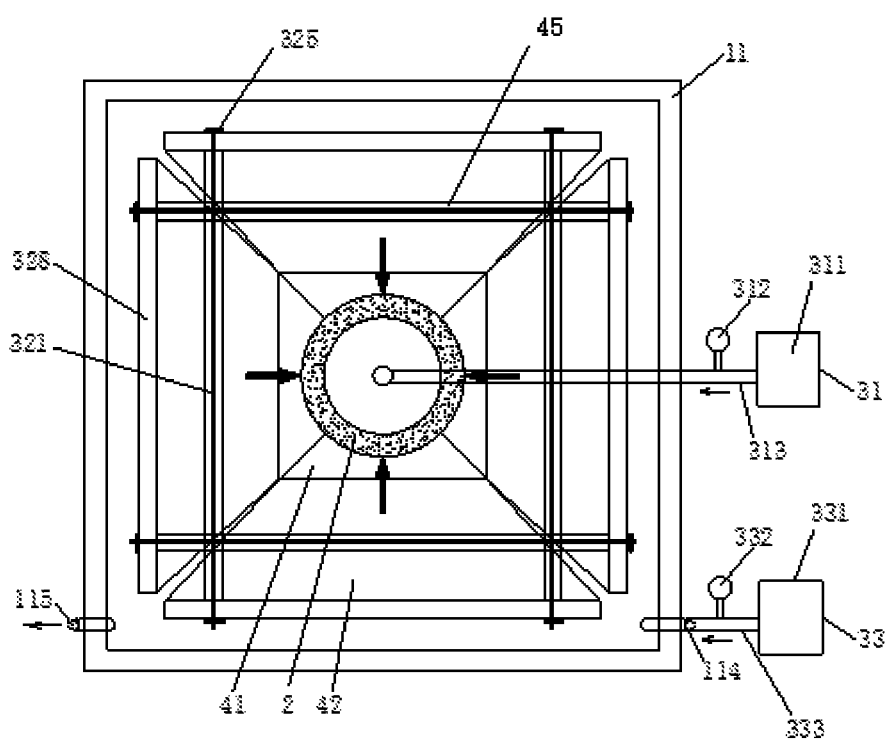
FIG. 9 is the top view structure diagram of the Experimental System in FIG. 2 after opening the upper cover plate and the sealing steel plate.
Figure 10:
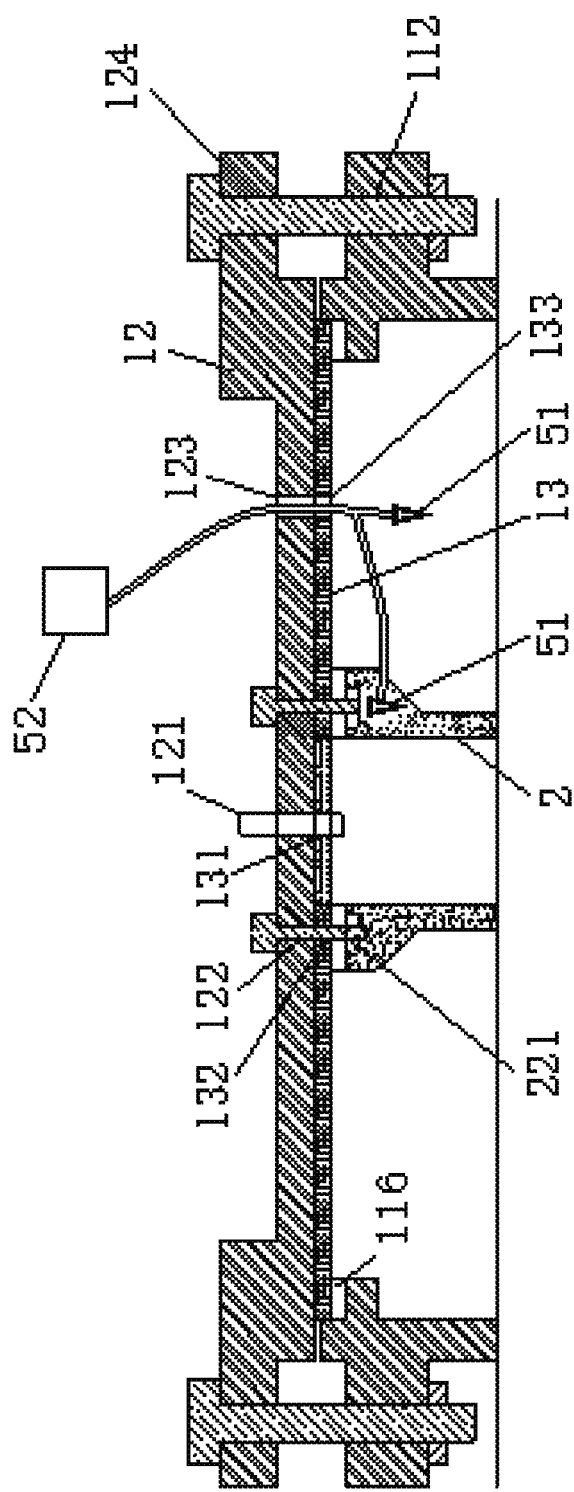
FIG. 10 is the axial sectional structure diagram of the opening end of the reaction wall in FIG. 2.

The disposable pervious concrete structure 41 is a cuboid structure attached to the outside of the lining structure 2, and the circulating pervious concrete structure 42 is a cuboid structure attached to the periphery of the disposable pervious concrete structure 41, and the concrete pouring formwork is specially processed. The formwork design is shown in FIG. 6. In the disposable pervious concrete structure 41, a lubrication layer 44 is respectively arranged between the first cushion layer and the first stress layer, and between the third stress layer and the second cushion layer; a mortar layer 43 is respectively arranged between the first stress layer and the second stress layer, and between the second stress layer and the third stress layer. In the circulating pervious concrete structure 42, a lubrication layer 44 is respectively arranged between the first cushion layer and the overall stress layer, and between the overall stress layer and the second cushion layer; the overall stress layer of the circulating pervious concrete structure 42 is located outside the first stress layer, the second stress layer and the third stress layer of the disposable pervious concrete structure 41. The mortar layer 43 is M7.5 mortar. The role of the mortar layer 43 is to connect the pervious concrete of the middle three layers into a whole, so that the force transmission is more uniform. The lubrication layer 44 is made of 1 mm thick galvanized steel plate, which aims to make the pervious concrete of the middle three layers more efficiently linked with the hydraulic steel sleeper.

In addition, two layers of horizontal # shaped steel strand duct 45 are reserved in the overall stressed layer of the circulating pervious concrete structure 42 from top to bottom, and the # shaped steel strand duct 45 are distributed around the lining structure 2. The left and right, front and back four directions of the # shaped steel strand duct 45 on each layer are respectively set at the quarter point of the circulating pervious concrete structure 42.

Preferably, When the circulating pervious concrete structure 42 is installed, an included angle of 5-10° is formed between the adjacent sides of the adjacent pervious concrete blocks, so that the four pervious concrete blocks in each layer form a trapezoidal platform with large upper part and small lower part, and the circulating pervious concrete structure 42 has a certain deformation buffer space in four directions.

Specifically, the prestress-loading mechanism 32 includes eight prestress steel strands 321 that run through the # shaped steel strand duct 45. The end of each prestressed steel strand 321 is fixed outside the heavy plate 328. The eight prestressed steel strands 321 are tensioned by the hydraulic tensioner 322, and the pressure is measured by the tension sensor 324 connected to the prestress steel strand 321; The hydraulic tensioner 322 is connected with an oil pressure gauge 326 and electric high-pressure oil pump 323 through an oil pipe 327.

Specifically, the lining structure 2 comprises hollow barrel 21 and flange plate 22 arranged at the upper and lower ends thereof. The hollow inner diameter of the hollow barrel 21 is the same as the inner diameter of the flange plate 22. The outer side of the hollow barrel 21 is provided with grouting zone 23 from the lower end to the upper end, and the outer diameter of the grouting zone 23 is the same as the outer diameter of the flange plate 22.

Preferably, the reaction wall 1 comprises a reaction wall body 11 of a three-dimensional hollow shell structure with an opening at one end and a boss on the inner wall of the opening, a rubber seal groove 116 is arranged on the boss along the periphery of the opening, a sealing steel plate 13 is matched and arranged in the rubber seal groove 116, an upper cover plate 12 is arranged outside the sealing steel plate 13, which is bolted to the reaction wall body 11, and the upper cover plate 12 is also connected with the sealing steel plate 13 by bolts; The center of the lower bottom surface of the inner cavity of the reaction wall body 11 is fixedly provided with a locating steel ring 111, and the inner diameter of the locating steel ring 111 is the same as the outer diameter of the flange plate 22.

Preferably, the outer peripheral wall of the reaction wall body 11 is provided with first stiffener 113 in a crisscross structure, and the outer edges around the opening end of the reaction wall body 11 are respectively provided with first bolt holes 112 for connecting with the upper cover plate 12; The center of the sealing steel plate 13 is provided with a water injection valve gate 131, second bolt holes 132 connected with the lining structure 2 is arranged around the water injection valve gate 131, and a second instrument cable outlet 133 is also arranged on one side of the water injection valve gate 131; The upper cover plate 12 comprises a second stiffener 125 in a crisscross structure arranged on the outer surface, a second water injection valve connector 121 corresponding to the water injection valve gate 131 is arranged at the center of the upper cover plate 12, third bolt holes 122 corresponding to the second bolt holes 132 is arranged around the second water injection valve connector 121, and a fourth instrument cable outlet 123 corresponding to the second instrument cable outlet 133 is arranged on one side of the second water injection valve connector 121, fourth bolt holes 124 corresponding to the first bolt holes 112 is also arranged at the peripheral edge of the upper cover plate 12; fifth bolt holes 221 corresponding to the second bolt holes 132 is arranged around the flange plate 22 at the upper end of the lining structure 2, and a rubber seal ring is used between the flange plate 22 at the upper end and the sealing steel plate 13 for sealing; The side wall of the reaction wall body 11 is provided with a first water injection valve connector 114, and the another side wall opposite to the first water injection valve connector 114 is provided with a drain valve connector 115.

Figure 3:
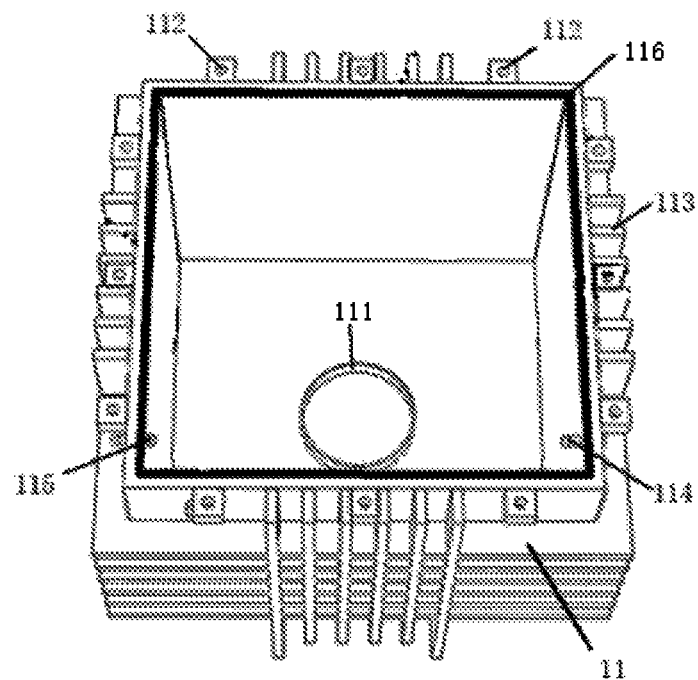
FIG. 3 is the structural diagram of the reaction wall body in FIG. 2.
Figure 4:
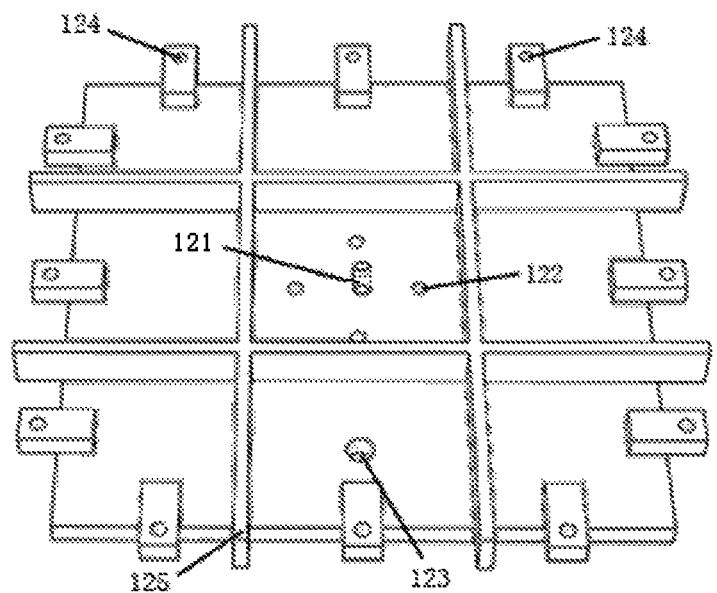
FIG. 4 is the structural diagram of the upper cover plate in FIG. 2.
Figure 5:
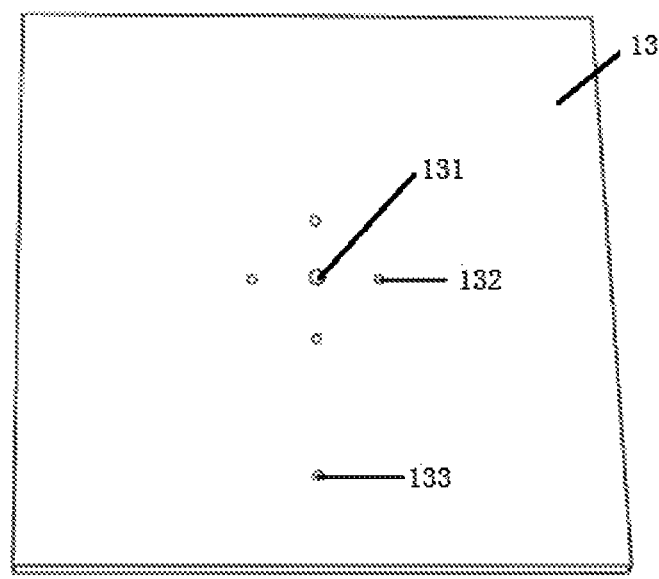
FIG. 5 is the structural diagram of the sealing steel plate in FIG. 2.

Specifically, the physical diagram of reaction wall 1 is shown in FIG. 3, and the internal contour dimension of reaction wall 1 is 1.2 m×1.2 m×1 m (long×wide×High), is formed by welding 50 mm thick steel plate, the steel used for reaction wall 1 is 45 # steel, with nominal yield strength not less than 355 MPa and tensile strength not less than 600 MPa. The sealing steel plate 13 is a 20 mm thick steel plate. As an additional sealing facility, the upper cover plate 12 is a cover plate made of a 50 mm thick steel plate. The locating steel ring 111 is welded at the center of the lower bottom surface of the inner cavity of the reaction wall body 11, and the inner diameter of the locating steel ring 111 is the same as the outer diameter of the flange plate 22.

The first stiffener 113 on the outer surface of the reaction wall body 11 is a 30 mm thick 100 mm wide steel bar with a spacing of 100 mm between the steel bar centerlines. The number of reinforcing steel bars is small due to the small force on the bottom. The outer edges around the opening end of the reaction wall body 11 are respectively provided with 8 pairs of first bolt holes 112 with a diameter of 32 mm for connecting with the upper cover plate 12. The locating steel ring 111 at the bottom of the cavity of the reaction wall body 11 is an annular steel sheet with a height of 50 mm and a thickness of 3 mm. The water inlet of the second water injection valve connector 121 at the center of the upper cover plate 12 and the water injection valve gate 131 at the center of the sealing steel plate 13 are holes with a diameter of 32 mm. The second stiffener 125 on the outer surface of the upper cover plate 12 is also a 30 mm thick and 100 mm wide steel bar, with the center line spacing of 100 mm. The water inlet of the first water injection valve connector 114 and the water outlet of the drain valve connector 115 are holes with a diameter of 32 mm.

The inner diameter of hollow barrel 21 is 200 mm, the outer diameter is 260 mm. The outer diameter of flange plate 22 is 360 mm. The thickness of hollow barrel 21 is gradually thickened to 360 mm after being less than 100 mm from its two ends, and the inner diameter remains unchanged at 200 mm.

The data acquisition instrument 52 includes a signal data acquisition system, a vibrating wire data recorder, and an optical fiber data recorder; The detector 51 embedded in the lining structure 2 includes: resistance strain gauge, optical fiber sensor, vibrating wire strain gauge; The detector 51 embedded in the surrounding rock layer 4 includes vibrating wire pore water pressure gauge and earth pressure gauge. All data lines of detector 51 are connected to the signal data acquisition system, vibrating wire data recorder and optical fiber data recorder after being led out, and a high-definition camera is erected at the center of the upper cover plate 12. All recorded data and images are summarized to the computer for processing and analysis.

For example, the monitoring scheme of the resistance strain gauge system is to monitor the strain of the reinforcement cage and lining concrete in the lining structure 2. Paste strain gauges on the three stirrups in the middle of the reinforcement cage (lower end stirrup, middle stirrup, upper end stirrup) every 90°, a total of 12 stirrup strain gauges; In addition, after the lining concrete has been cured for 28 days, the inner and outer walls of the concrete are divided into four layers (from top to bottom: the first layer, the second layer, the third layer, and the fourth layer). Each layer is pasted with four longitudinal and four transverse concrete strain gauges at 90° intervals, totaling 64 concrete strain gauges.

The experimental flow chart of the Experimental System of the present invention, as shown in FIG. 1, includes the following steps:

Step 1) Pour to form the lining structure 2 and surrounding rock layer 4 with the same height, including:

pouring the lining structure 2 includes: binding the reinforcement cage of lining structure 2 according to the design size; Pouring and curing of lining structure 2 with concrete meeting the required design strength; and embedding the detector 51 at the position to be detected in the lining structure 2;

Pouring the surrounding rock layer 4 includes: pouring the surrounding rock layer 4 into a specific shape and curing according to the design template, embedding the detector 51 at the position to be detected to be detected in the surrounding rock layer 4, reserving the # shaped steel strand duct 45 in the surrounding rock layer 4, and distributing the steel strand duct 45 around the lining structure 2.

Bind the reinforcement cage of lining structure 2 and arrange the detector 51 according to the design size. The reinforcement cage is composed of 8 longitudinal bars and 7 circular stirrups. The longitudinal bars and stirrups are made of Grade I steel (HPB300). The concrete meeting the required design strength is used for the pouring of lining structure 2, and the resistance strain gauge, optical fiber sensor and vibrating wire strain gauge is embedded at the position to be detected. Considering that the lining structure 2 is a thin-walled structure, with steel bars laid inside and a large number of strain gauges and signal transmission wires arranged, it is not easy to compact the concrete during pouring, but it is not allowed to vibrate with excessive strength, so C25 self-compacting concrete is used for pouring, the mix proportion is as shown in Table 1. During the lining concrete pouring, the forced mixer is used to mix the materials. The whole lining is placed on the vibration table for vibration. After the mixing, the lining concrete is poured within 20 minutes, and demoulded two days later, finally, standard curing lining concrete for 28 days. During concrete pouring, three 150 mm*150 mm*150 mm standard cubes are reserved to measure the compressive strength of materials, three 150 mm*150 mm*300 mm prism specimens are reserved to measure the elastic modulus of concrete, and three 150 mm (diameter)*300 mm cylinder specimens are reserved to measure the Poisson's ratio of concrete.

Step 2) Install the prestress-loading mechanism 32, the installation process is as follows: first, fix the cured lining structure 2, closely stick the disposable pervious concrete structure 41 in the inner ring of surrounding rock layer 4 to the outer wall of lining structure 2, then use mortar to make the layers of the disposable pervious concrete structure 41, and the outer wall of lining structure 2 closely combined to form a whole, after that, the circulating pervious concrete structure 42 of the outer ring of the surrounding rock layer 4 is closely attached to the outer wall of the disposable pervious concrete structure 41, and mortar masonry is used to closely combine the layers of the circulating pervious concrete structure 42 and the outer wall of the disposable pervious concrete structure 41 to form a whole.

After the disposable pervious concrete structure 41 and the circulating pervious concrete structure 42 are assembled, the high ductility ECC concrete is used to fill the gap between the lining and the surrounding rock as buffer layers, and the strain gauge on the outer wall of lining structure 2 is protected. See Table 2 for the benchmark mix proportion of the high ductility ECC concrete used. In addition, an included angle of 7° is formed between the adjacent sides of the adjacent pervious concrete blocks of the circulating pervious concrete structures 42. Thus, the circulating pervious concrete structures 42 has a certain deformation buffer space to better conduct and simulate the surrounding rock pressure to the lining structure 2; In addition, vibrating wire pore water pressure gauge and earth pressure gauge shall be embedded in surrounding rock layer 4.

The prestress-loading mechanism 32 includes eight prestress steel strands 321 running through the # shaped steel strand duct 45. The end of each prestress steel strand 321 is fixed outside the heavy plate 328 for force transmission. The heavy plate 328 is attached to the outside of the overall stress layer of the circulating pervious concrete structure 42. The eight prestress steel strands 321 are tensioned through the hydraulic tensioner 322, the pressure is measured by the tension sensor 324 connected to the prestress steel strand 321; The hydraulic tensioner 322 is connected with oil pressure gauge 326 and electric high-pressure oil pump 323 through oil pipe 327. After the mortar solidifies, four heavy plates 328 are respectively attached to the outside of the overall stress layer of the circulating pervious concrete structure 42, flush with the sides of the first cushion layer and the second cushion layer, and drill holes on the heavy plate 328 corresponding to the extension of the prestress steel strand 321; Pass four prestress steel strands 321 through the # shaped steel strand duct 45 reserved in the surrounding rock layer 4, and fix the end of each prestress steel strand 321 outside the heavy plate 328; The prestress steel strand 321 is tensioned by the hydraulic tensioner 322 and the electric high-pressure oil pump 323. When the predetermined tensile stress is reached, the two ends of the prestress steel strand 321 are fixed by the anchorage 325 to keep the pressure of the prestress steel strand 321 on the lining structure 2 model stable, so as to simulate the pressure effect of the tunnel surrounding rock.

Step 3) Lift the whole body formed by lining structure 2 and surrounding rock layer 4 together with prestress steel strand 321 vertically into the inner cavity of reaction wall 1, and insert the bottom of lining structure 2 into locating steel ring 111. The process is: first, lay a layer of dense mortar in the locating steel ring 111 at the bottom of the inner cavity of the reaction wall body 11, then place the lining structure 2 on the mortar, shake it manually to make the bottom lining structure 2 contact with the mortar closely, and adjust the geometric position and levelness of the lining structure 2.

Step 4) Install and seal the upper cover plate 12, including: install a rubber seal ring at the boss of the opening of the reaction wall body 11 and the top of the lining structure 2; cover the upper cover plate 12 on the sealing steel plate 13, connect the lining structure 2 with the sealing steel plate 13 and the upper cover plate 12 by bolts, and connect the reaction wall body 11 with the upper cover plate 12 by bolts; In addition, the data line of detector 51 embedded in lining structure 2 and the data line of detector 51 embedded in surrounding rock layer 4 are led out through the second instrument cable outlet 133 of the sealing steel plate 13 and the fourth instrument cable outlet 123 of the upper cover plate 12.

Step 5) Install the external water pressure loading mechanism 33, including: install the second pipe 333 on the first water injection valve connector 114 outside the reaction wall body 11, and install the second booster pump 331 and the second water pressure gauge 332 on the other end of the second pipe 333.

Step 6) Install the internal water pressure loading mechanism 31, including: install the first pipe 313 on the second water injection valve connector 121 outside the upper cover plate 12, and install the first booster pump 311 and the first water pressure gauge 312 on the other end of the first pipe 313.

Step 7) load the external water pressure; before loading the external water pressure, the main problem is the sealing of the external pressure chamber. Fill the inside of reaction wall 1 with water, and use the second booster pump 331 outside to automatically carry out.

First, seal the second instrument cable outlet 133 and the fourth instrument cable outlet 123, pierce the middle part of the cone type rubber plug, pass the instrument cable through, fill the hole with glass glue, and then plug the rubber plug upwards from the bottom of the sealing steel plate 13. The top of the rubber plug reaches the center of the instrument cable outlet, and then the instrument cable is sheathed in a PVC pipe with a diameter slightly larger than the instrument cable. The inside of the PVC pipe is filled with epoxy resin.

Finally, seal the sealing steel plate 13 around, and the connection between the sealing steel plate 13 and the reaction wall body 11 is fully welded.

Open the second booster pump 331 and the first water injection valve connector 114 on the reaction wall body 11, and inject water into the external pressure chamber until the drain valve connector 115 starts to discharge water, indicating that the external pressure chamber has been filled with water. At this time, close the second booster pump 331, close the drain valve connector 115, and turn on the detector 51 to start recording. According to the experimental scheme, open the second booster pump 331 to inject water and pressurize it to the design value of water pressure, and use the data acquisition instrument 52 to collect data.

Step 8) load the internal water pressure; before loading the internal water pressure, the main problem is the sealing of the internal water injection pressure chamber. After the water injection pressure chamber is sealed, fill the inner chamber of lining structure 2 with water, and use the first booster pump 311 outside to automatically carry out.

First, seal the bottom of lining structure 2. When lining structure 2 is installed, a mortar layer has been laid at its bottom. Considering the high water pressure required by the experiment, 50 mm thick epoxy resin is poured into the hollow barrel 21 for sealing.

The inner wall and top of lining structure 2 shall also be sealed. In order to simulate the waterproof layer of lining structure 2, a PVC pipe with a diameter slightly smaller than the inner diameter of lining structure 2 is placed in lining structure 2, and then epoxy resin is filled between the inner wall of lining structure 2 and the PVC pipe. A rubber pad with a thickness of 2 mm is laid between the top of lining structure 2 and sealing steel plate 13. After covering the upper cover plate 12, epoxy resin is filled between it and PVC pipe.

Open the first booster pump 311 to inject water into the internal water injection pressure chamber formed between the inner wall of lining structure 2 and reaction wall 1, until the pressure is stable, and then stop pressurizing. At this time, the inner chamber of lining structure 2 has been filled with water, open the second water injection valve joint 121 to make the initial water pressure 0, and turn on the detector 51 to start recording. According to the experimental scheme, open the first booster pump 311, start loading to the design value according to the loading scheme, and use the data acquisition instrument 52 to collect data.

Step 9) Connect the data line of the detector 51 to the data acquisition instrument 52 for data acquisition, and then connect it to the computer. Through the data acquisition software, collect and post process the collected stress and strain, pressure of prestress steel strand 321, internal and external water pressure and other data, and analyze the stability of surrounding rock layer 4 under different pressure loads and the stress and strain relationship between steel bars and concrete in lining structure 2. After the experiment, open the upper cover plate 12 and the sealing steel plate 13, pump out the water in the internal water injection pressure chamber and the external pressure chamber respectively, and observe the broken appearance of the surrounding rock layer 4 and the lining structure 2.

TABLE 1

| Materials | Cement | Fly ash | Water | Sand | Guarmi stone |
|---|---|---|---|---|---|
| Mix Proportion | 1 | 0.428 | 0.585 | 2.289 | 3.224 |

TABLE 2

| Materials | Cement | Fly ash | Quartz sand | Water | Water reducing agent | PVA |
|---|---|---|---|---|---|---|
| consumption (kg)/m$^3$ | 450 | 854 | 469 | 326 | 0.68 | 26 |

The above is only a preferred embodiment of the invention and is not intended to limit the invention. Any modification, equivalent replacement, improvement, etc. made within the spirit and principle of the invention shall be included in the protection scope of the invention.

What is claimed is:

1. An experimental system of surrounding rock and lining structure under unequal surrounding rock pressure and water pressure, comprising:

reaction wall with a three-dimensional hollow shell structure; a center of an inner cavity of the reaction wall is provided with a vertically arranged hollow cylindrical lining structure, and a height of the lining structure is same as a height of the inner cavity of the reaction wall, so that a circumferential inner wall of the reaction wall and an outer wall of the lining structure form an external pressure chamber, and an inner top and inner bottom of the reaction wall and an inner wall of the lining structure form an internal water injection pressure chamber;

the outer wall of the lining structure is provided with a surrounding rock layer of pervious concrete structure; a prestress-loading mechanism is arranged inside the surrounding rock layer; the prestress-loading mechanism consists of prestress steel strand, which compresses the surrounding rock layer in four directions, left and right, front and back through the prestress steel strand, to simulate an effect of the unequal surrounding rock pressure;

the surrounding rock layer is arranged with a disposable pervious concrete structure and a circulating pervious concrete structure from an inside to an outside;

the disposable pervious concrete structure is a cuboid structure attached to the outside of the lining structure, and the circulating pervious concrete structure is a cuboid structure attached to an outside of the disposable pervious concrete structure;

the disposable pervious concrete structure comprises a first cushion layer, a first stress layer, a second stress layer, a third stress layer and a second cushion layer arranged from a lower end to an upper end; a lubrication layer is respectively arranged between the first cushion layer and the first stress layer, and between the third stress layer and the second cushion layer of the disposable pervious concrete structure; a mortar layer is respectively arranged between the first stress layer and the second stress layer, and between the second stress layer and the third stress layer of the disposable pervious concrete structure;

the circulating pervious concrete structure comprises a first cushion layer, an overall stress layer and a second cushion layer arranged from the lower end to the upper end; a lubrication layer is respectively arranged between the first cushion layer and the overall stress layer, and between the overall stress Layer and the second cushion layer of the circulating pervious concrete structure; the overall stress layer of the circulating pervious concrete structure is located outside the first stress layer, the second stress layer and the third stress layer of the disposable pervious concrete structure; two # shaped steel strand channels are chiseled inside the overall stress layer of the circulating pervious concrete structure, which are arranged in two layers; the outer wall of the overall stress layer of the circulating pervious concrete structure is bonded with heavy plate for force transmission;

an external water pressure loading mechanism is also arranged outside an opening end of the reaction wall; the surrounding rock layer and the lining structure are applied with external water pressure in a direction of periphery to the center of the lining structure via the external water pressure loading mechanism, to simulate an effect of the external water pressure; an internal water pressure loading mechanism is arranged on the reaction wall corresponding to an upper end of the hollow cylinder of the lining structure; the internal water pressure loading mechanism is used to inject water into the internal water injection pressure chamber for pressurization, to simulate an effect of an internal water pressure;

the experimental system also includes a monitoring device embedded in the surrounding rock layer and lining structure respectively; the monitoring device is used to collect and analyze the following data: a surrounding rock pressure in the surrounding rock layer, an internal and external water pressure, and a stress and strain in the lining structure.

2. The experimental system of claim 1, wherein the prestress-loading mechanism includes eight prestress steel strands running through the # shaped steel strand duct; the end of each prestress steel strand is fixed outside the heavy plate for force transmission; the eight prestress steel strands are tensioned through a hydraulic tensioner, a pressure applied by the hydraulic tensioner is measured by an tension sensor connected to the prestress steel strand; the hydraulic tensioner is connected with oil pressure gauge and electric high-pressure oil pump through oil pipe.

3. The experimental system of claim 2, wherein the lining structure comprises hollow barrel and flange plate arranged at the upper and lower ends thereof; the hollow inner diameter of the hollow barrel is the same as the inner diameter of the flange plate; the outer side of the hollow barrel is provided with grouting zone from the lower end to the upper end, and the outer diameter of the grouting zone is the same as the outer diameter of the flange plate.

4. The experimental system of claim 3, wherein the reaction wall comprises a reaction wall body of a three-dimensional hollow shell structure with an opening at one end and a boss on the inner wall of the opening, a rubber seal groove is arranged on the boss along the periphery of the opening, a sealing steel plate is matched and arranged in the rubber seal groove, an upper cover plate is arranged outside the sealing steel plate, which is bolted to the reaction wall body, and the upper cover plate is also connected with the sealing steel plate by bolts; the center of the lower bottom surface of the inner cavity of the reaction wall body is fixedly provided with a locating steel ring, and the inner diameter of the locating steel ring is the same as the outer diameter of the flange plate.

5. The experimental system of claim 4, wherein the outer peripheral wall of the reaction wall body is provided with first stiffener in a crisscross structure, and the outer edges around the opening end of the reaction wall body are respectively provided with first bolt holes for connecting with the upper cover plate; the center of the sealing steel plate is provided with a water injection valve gate, second bolt holes connected with the lining structure is arranged around the water injection valve gate, and a second instrument cable outlet is also arranged on one side of the water injection valve gate; the upper cover plate comprises a second stiffener in a crisscross structure arranged on the outer surface, a second water injection valve connector corresponding to the water injection valve gate is arranged at the center of the upper cover plate, third bolt holes corresponding to the second bolt holes is arranged around the second water injection valve connector, and a fourth instrument cable outlet corresponding to the second instrument cable outlet is arranged on one side of the second water injection valve connector, fourth bolt holes corresponding to the first bolt holes is also arranged at the peripheral edge of the upper cover plate; fifth bolt holes corresponding to the second bolt holes is arranged around the flange plate at the upper end of the lining structure, and a rubber seal ring is used between the flange plate at the upper end and the sealing steel plate for sealing; the side wall of the reaction wall body is provided with a first water injection valve connector, and the another side wall opposite to the first water injection valve connector is provided with a drain valve connector.

6. An experimental method of the experimental system of claim 5, comprising the following steps:
   step 1) pour to form the lining structure and surrounding rock layer with the same height, including:
   pouring the lining structure includes: binding a reinforcement cage of lining structure according to a design size; pouring and curing of lining structure with concrete meeting a required design strength; and embedding a detector at a position to be detected in the lining structure;
   pouring the surrounding rock layer includes: pouring the surrounding rock layer into a specific shape and curing according to a design template, embedding the detector at the position to be detected in the surrounding rock layer, reserving the # shaped steel strand duct in the surrounding rock layer, and distributing the # shaped steel strand duct around the lining structure;
   step 2) install the prestress-loading mechanism, including: first fix the lining structure that has been poured and cured, and then closely stick the surrounding rock layer that has been poured and cured to the outer wall of the lining structure and building with mortar; after the mortar is solidified, embed four heavy plates for force transmission around the surrounding rock layer; and drill holes on the heavy plate corresponding to an extension of the prestress steel strand; pass four prestress steel strands through the # shaped steel strand duct reserved in the surrounding rock layer, and fix an end of each prestress steel strand outside the heavy plate; tension the prestress steel strand through the hydraulic tensioner and the electric high-pressure oil pump, and fix both ends of the prestress steel strand with the anchorage when the predetermined tensile stress is reached;
   step 3) lift the whole body formed by the lining structure and the surrounding rock layer together with the prestress steel strand vertically into the inner cavity of the reaction wall, and insert a bottom of the lining structure into the locating steel ring;
   step 4) install and seal the upper cover plate, including: install a rubber seal ring at a boss of the opening of the reaction wall body and a top of the lining structure; cover the upper cover plate on the sealing steel plate, connect the lining structure with the sealing steel plate and the upper cover plate by bolts, and connect the reaction wall body with the upper cover plate by bolts; in addition, a data line of detector embedded in the lining structure and a data line of detector embedded in the surrounding rock layer are led out through the second instrument cable outlet of the sealing steel plate and the fourth instrument cable outlet of the upper cover plate;
   step 5) install the external water pressure loading mechanism, including: install one end of a second pipe on the first water injection valve connector outside the reaction wall body, and install a second booster pump and a second water pressure gauge on the other end of the second pipe;
   step 6) install the internal water pressure loading mechanism, including: install one end of a first pipe on the second water injection valve connector outside the upper cover plate, and install a first booster pump and a first water pressure gauge on the other end of the first pipe;
   step 7) load the external water pressure, including: seal the second instrument cable outlet, the fourth instrument cable outlet and the sealing steel plate around; according to an experimental scheme, open the second booster pump to inject water into the external pressure chamber formed between the circumferential inner wall of reaction wall and the outer wall of lining structure;
   step 8) load the internal water pressure, including: seal the lining structure; according to the experimental scheme, open the first booster pump to inject water into the internal water injection pressure chamber formed between the inner wall of lining structure and reaction wall, until the water pressure reaches a set design value, use the data acquisition instrument to collect data;
   step 9) connect the data line of the detector to the data acquisition instrument for data acquisition, and then connect it to a computer; through a data acquisition software, collect and post process collected stress and strain, pressure of prestress steel strand, internal and external water pressure, and analyze stability of surrounding rock layer under different pressure loads and stress and strain relationship between steel bars and concrete in the lining structure.

7. The experimental method of claim 6, wherein in the step 8), the second instrument cable outlet and the fourth instrument cable outlet are filled and sealed with epoxy resin; and the connection between the sealing steel plate and the reaction wall body is fully welded.

8. The experimental method of claim 7, wherein the bottom of the lining structure is sealed by pouring 40-60 mm thick epoxy resin at the bottom of the lining structure; the inner wall of the lining structure is sealed by placing PVC pipe in the lining structure, and then filling epoxy resin between the inner wall of the lining structure and the PVC pipe; a diameter of the PVC pipe is slightly smaller than the inner diameter of the lining structure.

* * * * *